United States Patent
Filiberti et al.

(10) Patent No.: US 8,090,074 B2
(45) Date of Patent: Jan. 3, 2012

(54) SYSTEMS AND METHODS FOR OBTAINING RECONSTRUCTED IMAGES DURING A TREATMENT SESSION

(75) Inventors: Reto W. Filiberti, Steinhausen (CH); Patrik Kunz, Baden (CH); Daniel Morf, Buch am Irchel (CH)

(73) Assignee: Varian Medical Systems International AG, Zug (CH)

( * ) Notice: Subject to any disclaimer, the term of this patent is extended or adjusted under 35 U.S.C. 154(b) by 152 days.

(21) Appl. No.: 12/573,030

(22) Filed: Oct. 2, 2009

(65) Prior Publication Data

US 2011/0080990 A1    Apr. 7, 2011

(51) Int. Cl.
*A61B 6/03* (2006.01)
(52) U.S. Cl. ............................................. 378/65; 378/62
(58) Field of Classification Search ................... 378/62, 378/65
See application file for complete search history.

(56) References Cited

U.S. PATENT DOCUMENTS

2004/0005027 A1 *  1/2004  Nafstadius ................... 378/65
2006/0064008 A1     3/2006  Moore

* cited by examiner

*Primary Examiner* — Hoon Song
(74) *Attorney, Agent, or Firm* — Vista IP Law Group, LLP

(57) ABSTRACT

A medical system includes a treatment radiation source configured to deliver treatment radiation during a treatment session, an imaging system configured to obtain image data during the treatment session, and a processor configured to determine a beam break, and automatically operate the imaging system to obtain the image data during the beam break. A medical system includes a treatment radiation source, an imaging system configured to automatically obtain image data in a beam break that occurs during a treatment session, and a processor configured to automatically operate the treatment radiation source to deliver treatment radiation during the treatment session after the beam break ends.

33 Claims, 11 Drawing Sheets

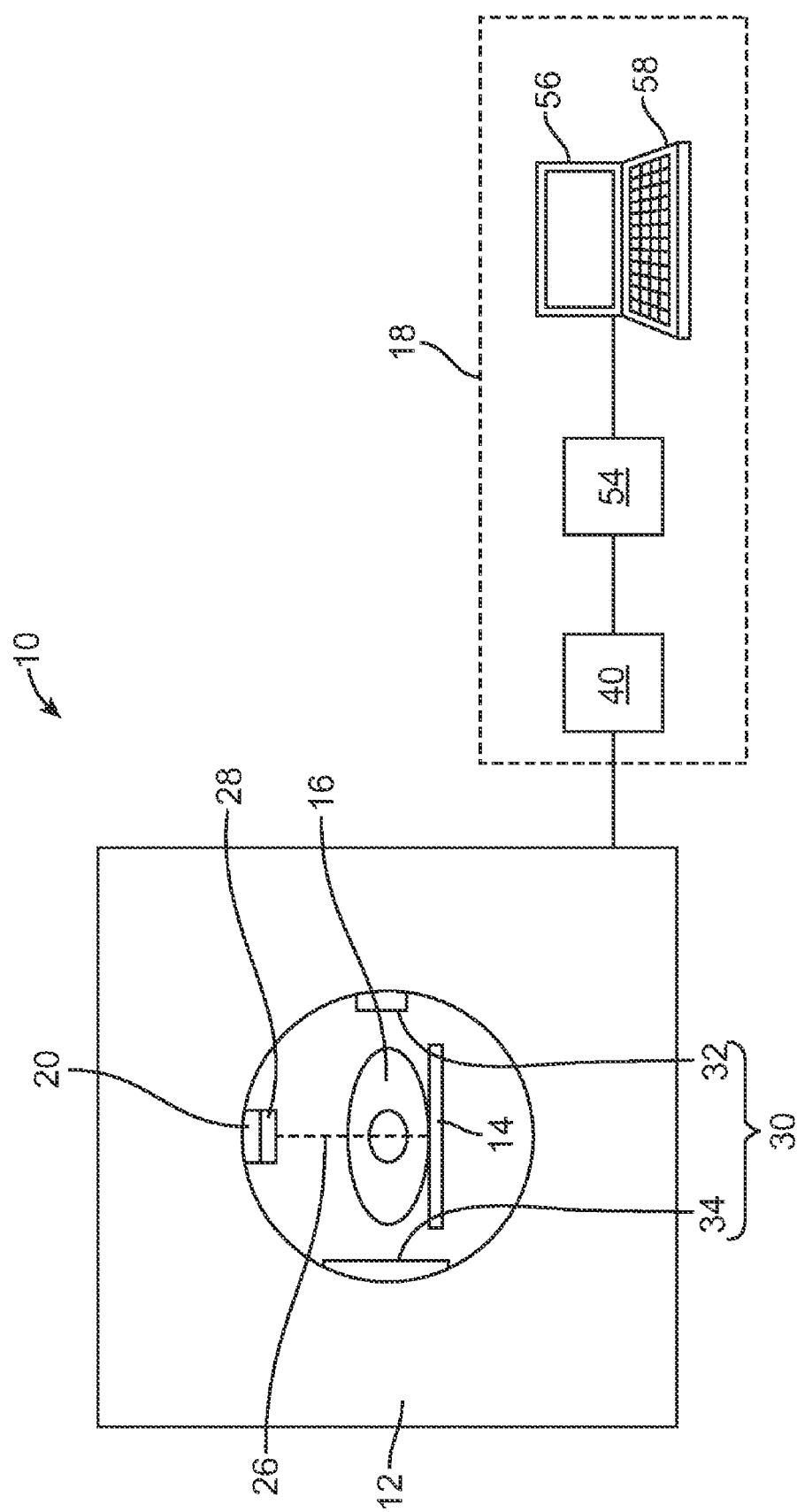

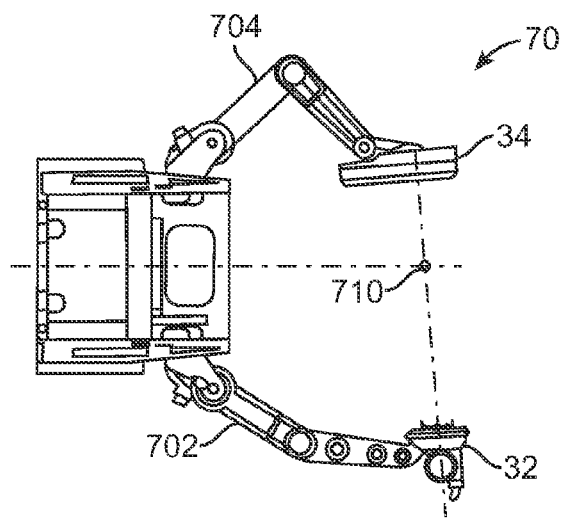
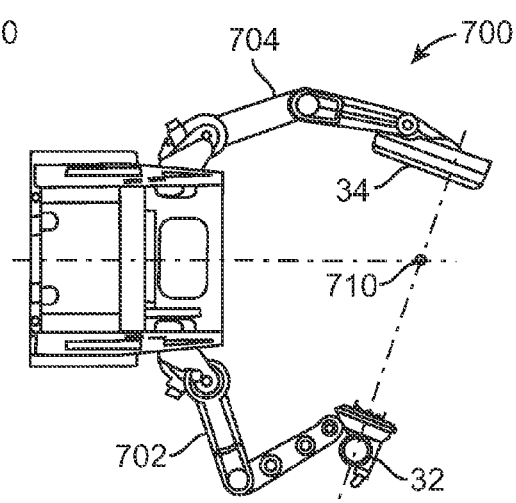
FIG. 7A　　　　　　　　FIG. 7B
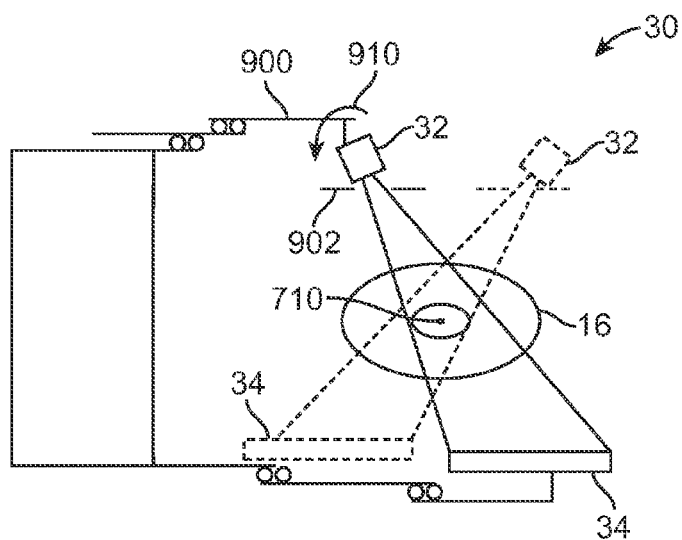
FIG. 8

US 8,090,074 B2

SYSTEMS AND METHODS FOR OBTAINING RECONSTRUCTED IMAGES DURING A TREATMENT SESSION

FIELD

This application relates generally to medical imaging, and more specifically, to systems and methods for performing an imaging procedure during treatment.

BACKGROUND

Radiation has been employed to image and treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes, in a radiation treatment procedure, a plurality of treatment sessions may be performed. In each treatment session, a radiation source may be placed at one or more prescribed gantry angles to thereby deliver radiation beam towards a target tissue from certain prescribed angles. As a result of delivering radiation towards the target tissue from a plurality of different angles, a sufficient radiation dose may be delivered to the target tissue to thereby treat the target tissue, while surrounding healthy tissue may be protected.

In some cases, before a radiation treatment session is performed, an image of the target region may be obtained to verify the shape and location of the target region. After a treatment session is performed, an image of the target region may also be obtained again to verify that the dosage was correctly delivered during the treatment session. Inventor of the subject application determines that it is desirable to have an efficient technique for obtaining reconstructed image during a treatment session.

SUMMARY

In accordance with some embodiments, a medical system includes a treatment radiation source configured to deliver treatment radiation during a treatment session, an imaging system configured to obtain image data during the treatment session, and a processor configured to determine a beam break, and automatically operate the imaging system to obtain the image data during the beam break.

In accordance with other embodiments, medical system includes a treatment radiation source, an imaging system configured to automatically obtain image data in a beam break that occurs during a treatment session, and a processor configured to automatically operate the treatment radiation source to deliver treatment radiation during the treatment session after the beam break ends.

In accordance with other embodiments, a medical system includes a treatment radiation source configured to deliver treatment radiation during a treatment session, an imaging system configured to obtain image data during the treatment session, and a processor configured for reconstruction of an image using at least some of the image data during the treatment session.

In accordance with other embodiments, an imaging method includes obtaining image data during a treatment session, and reconstructing an image using at least some of the image data during the treatment session.

In accordance with other embodiments, a medical system includes means for delivering treatment radiation during a treatment session, means for obtaining image data during the treatment session, and means for reconstructing an image using at least some of the image data during the treatment session. The images acquired during the treatment session may be used during and/or after the treatment session.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 1A illustrates a radiation system in accordance with some embodiments;

FIGS. 7A and 7B illustrate an imaging system in accordance with some embodiments;

FIG. 8 illustrates an imaging system in accordance with other embodiments;

DESCRIPTION OF THE EMBODIMENTS

Figure 1B:
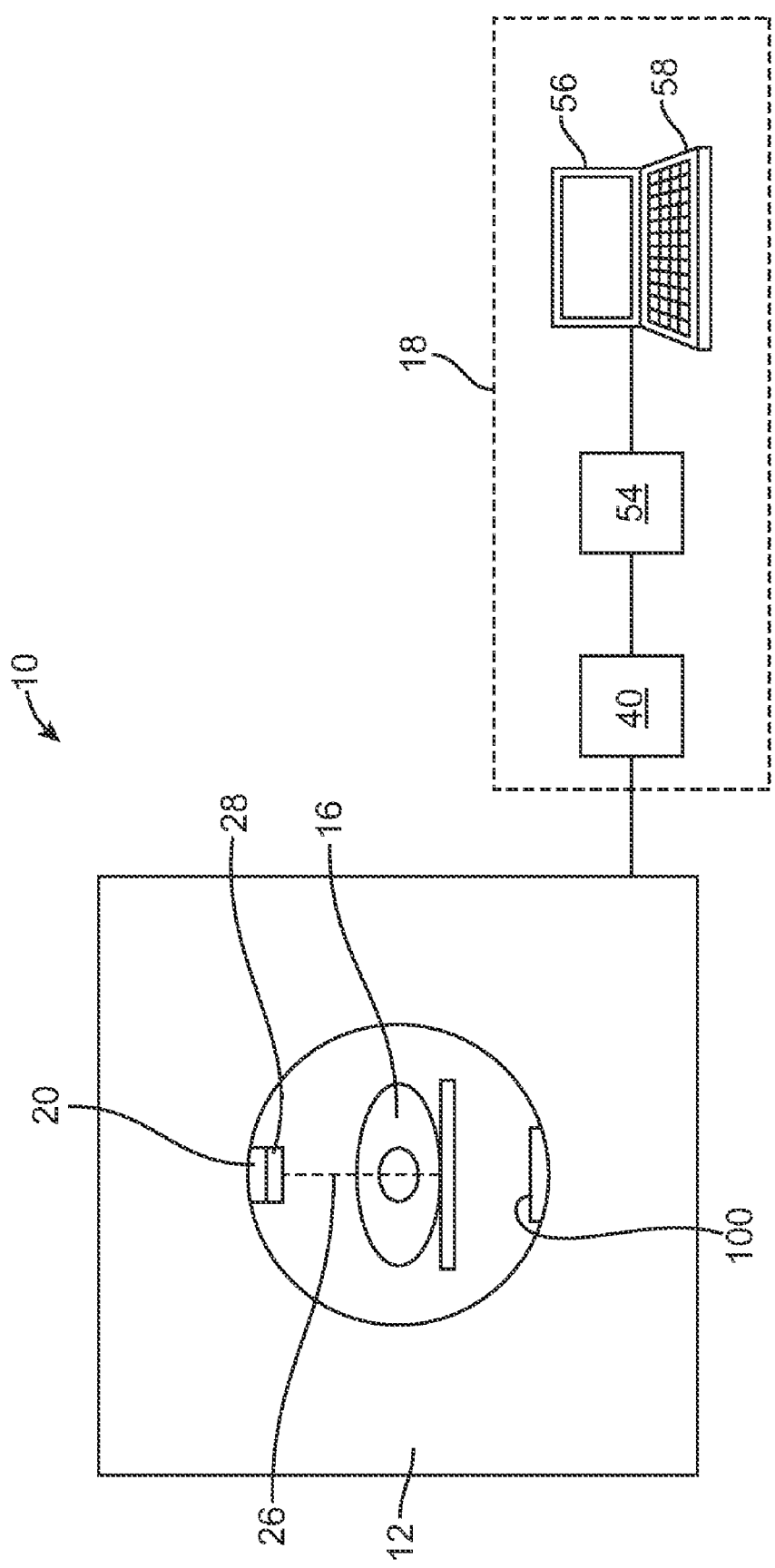
FIG. 1B illustrates a radiation system in accordance with other embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1A illustrates a radiation system 10 that includes an imaging system 30 for acquiring image(s) during a treatment session in accordance with some embodiments. The system 10 includes a gantry 12, a patient support 14 for supporting a patient 16, and a control system 18 for controlling an operation of the gantry 12. The system 10 also includes a radiation source 20 that projects a beam 26 of radiation towards a patient 16 while the patient 16 is supported on support 14, and a collimator system 28 for controlling a delivery (e.g., shape and/or aiming) of the radiation beam 26. For example, in some embodiments, the collimator system 28 may include a plurality of leaves for changing a shape of the beam 26. In other embodiments, the collimator system 28 may be rotatable (e.g., relative to an axis of the beam 26). The radiation source 20 can be configured to generate a cone beam, a fan beam, or other types of radiation beams, such as a scanning beam, in different embodiments.

In the illustrated embodiments, the radiation source 20 is a treatment radiation source for providing treatment energy. In the illustrated embodiments, the radiation source 20 is coupled to the gantry 12, and is located within a bore defined by the gantry 12.

As shown in the figure, the system 10 also has an imaging system 30 configured for obtaining image data during a treatment session. The imaging system 30 includes an x-ray source 32 and an imager 34 located at an operative position relative to the x-ray source 32. The x-ray source 32 is configured to deliver diagnostic radiation having an energy range that is suitable for imaging at least a part of the patient 16. During use, the x-ray source 32 delivers a radiation beam towards the patient 16, and radiation exiting from the patient 16 is received by the imager 34. The imager 34 generates image data in response to the received radiation. In some embodiments, the imager 34 may include a layer of scintillating material for converting radiation into photons, and a circuit layer for converting the photons into electrical signals. In other embodiments, the imager 34 may include a conversion layer between two electrode layers, wherein the conversion layer is configured to generate electron-hole pairs in response to radiation received by the imager 34. In some cases, the imager 34 may be implemented using a flat panel. The imager 34 is coupled to a processor 54, and is configured to transmit image data to the processor 54 for processing (e.g., reconstruction of image data during a treatment session). Alternatively, instead of the processor 54, the imager 34 may transmit image data to another processor for processing. As used in this specification, the term "processor" may refer to one or more processing units, wherein each processing unit may be implemented using a processing device. Thus, the term "processor" may refer to one processor, or more than one processor including multiprocessor systems and one or more processors in multiple systems. In the illustrated embodiments, the x-ray source 32 and the imager 34 of the imaging system 30 are mounted to a same gantry 12 to which the radiation source 20 is also mounted. Thus, rotation of the gantry 12 will cause the x-ray source 32 and the radiation source 20 to rotate together. In other embodiments, the x-ray source 32 and the imager 34 may be mounted to a second gantry that is different from the gantry 12. In such cases, the movement of the x-ray source 32 and the imager 34 may be independent from the radiation source 34. It should be noted that any of the components shown in FIG. 1A may be considered to be a part of the imaging system 30 in other embodiments.

In the illustrated embodiments, the control system 18 includes the processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure. In such case, the gantry 12 may be fixed, and the patient support 14 is rotatable and/or translatable (e.g., with respect to one or more axes). The operation of the radiation source 20, the collimator system 28, and the gantry 12 (if the gantry 12 is rotatable), are controlled by the control 40, which provides power and timing signals to the radiation source 20 and the collimator system 28, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. Also, in other embodiments, in addition to being a treatment radiation source, the radiation source 20 can also be a diagnostic radiation source for providing diagnostic energy. In such cases, the system 10 will include an imager, such as the imager 100, located at an operative position relative to the source 20 (e.g., under the support 14)(FIG. 1B). In further embodiments, the treatment source may be used for imaging provided that the system 10 includes a suitable imager (e.g., one that is configured to generate image signals in response to treatment radiation energy). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV.

In other embodiments, the radiation source 20 of the system 10 may have different ranges of motions and/or degrees of freedom. For example, in other embodiments, the radiation source 20 may be rotatable about the patient 16 completely through a 360° range (e.g., one or multiple rotations), or partially through a range that is less than 360°. Also, in other embodiments, the radiation source 20 is translatable relative to the patient 16. In further embodiments, the source 20 may be coupled to the gantry 12 via an arm, in which case, the source 20 is located outside the bore of the gantry 12. In such cases, the collimator may optionally be configured to tilt in one or more axes.

Although the above embodiments have been described with reference to delivering treatment radiation that is in the form of x-rays, in other embodiments, the system and technique described herein may be used for other types of treatment energy. For examples, in other embodiments, the radiation source 20 may be a proton source (in which case, the radiation system 10 is a proton system) for delivering protons to treat a patient, an electron source for delivering electrons, or other types of particle source for delivering other types of particles for treating patient. In further embodiments, the radiation source 20 may provide Cobalt or Gamma radiation. Accordingly, embodiments of the system and method described herein may be used in other types of treatment, such as proton treatment, which may be considered to be a type of radiation treatment. Also, it should be noted that the term "collimator" is not limited to a device having leaves for blocking radiation, and may refer to a device having one or more jaws or jaw blocks. Thus, a position of a collimator may refer to position of leaves of a collimator, position of collimator jaws, or a global position of the collimator itself relative to some coordinate system (e.g., a position of the collimator relative to a gantry or relative to a radiation machine, etc.). In other embodiments, instead of collimators, scanning beam technique may be used, such as for electron beam or other types of particle beam.

Figure 2:
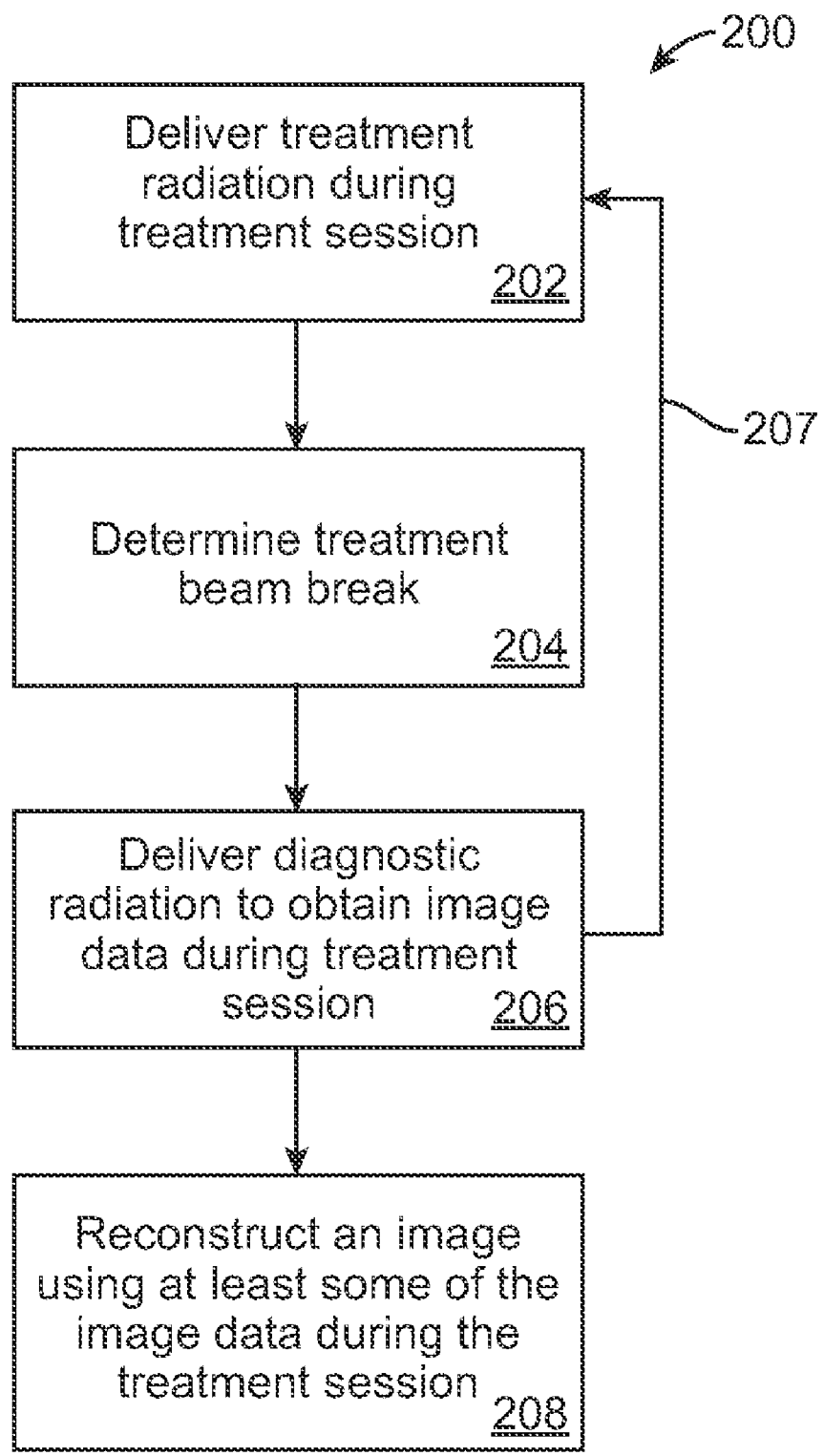
FIG. 2 illustrates a method of performing an imaging procedure during a treatment session in accordance with some embodiments.

FIG. 2 illustrates a method 200 for obtaining an image during a treatment session in accordance with some embodiments. As used in this specification, the term "treatment session" refers to a procedure during which a patient is being treated. The procedure may be performed within a certain period, such as, within a day, several hours, several minutes, or other duration of time. In some embodiments, the patient remains in a treatment room and/or on a patient support (e.g., support 14) during the treatment session. The method 200 will be described with reference to the system 10 of FIG. 1. However, it should be noted that the method 200 may be performed using other systems in other embodiments.

First, the system 10 is operated to deliver treatment radiation during a treatment session (Step 202). In some embodiments, such may be accomplished by obtaining a treatment plan, and executing the treatment plan using the system 10. For example, the processor 54 may receive the treatment plan, e.g., in a form of an electronic file. The received treatment plan may include a complete plan for treatment, a part of the plan for treatment (such as one or more parameters), or information derived from the plan. In other embodiments, the act of obtaining the treatment plan may be performed by the processor 54 retrieving the treatment plan from a medium, such as a memory. In the illustrated embodiments, in response to the processor 54 processing the treatment plan, the radiation system 10 is operated to deliver radiation towards a target region in the patient 16. Such may be accomplished by the processor 54 generating one or more control signals to operate the radiation source 20, the collimator 28, the gantry 12, the patient support 14, or any combination of the foregoing. The radiation system 10 may rotate the radiation source 20, move the collimator leaves, move the patient support 14, or any combination of the foregoing. In some embodiments, the moving of the collimator leaves is performed to adjust a shape of the beam 26 such that the beam 26 corresponds (e.g., conforms) to a shape of the target region. In other embodiments, the moving of the collimator leaves is performed to adjust a shape of the beam 26 such that a portion of a target region receives relatively more radiation than another portion of the target region, as in an intensity-modulated radiation therapy (IMRT).

Figure 4A:
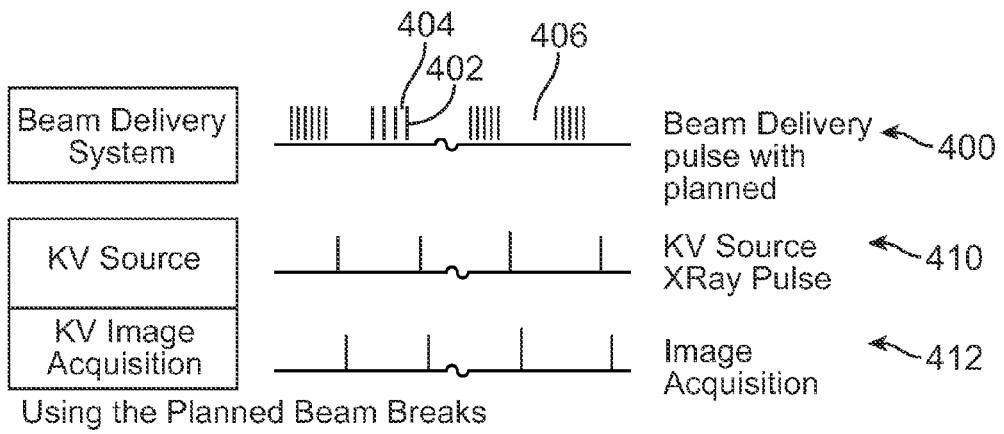
FIG. 4A illustrates a technique for acquiring image data during a treatment session using planned beam breaks.

Returning to FIG. 2, next the processor 54 determines a treatment beam break (Step 204). As used in this specification, the term "beam break" refers to a condition in which no treatment radiation is being delivered. Also, as used in this specification, the term "treatment beam break" or "planned beam break" refers to a beam break that is such as a beam break that is incorporated in a treatment plan. In the illustrated embodiments, the processor 54 is configured to determine the treatment beam break by processing the treatment plan, which prescribes when radiation is to be delivered or not. FIG. 4A illustrates an example of a treatment beam pulse chart 400, which may be derived from a treatment plan. As shown in the figure, the treatment beam pulses 402 represent treatment beam that is prescribed in the treatment plan to be delivered at certain gantry angles. Any of the regions (such as region 404 that is between treatment beam pulses, or region 406 that is between groups of treatment beam pulses) that does not include a treatment beam pulse may represent a treatment beam break. In any of the embodiments described herein, the treatment beam break(s) may be stored in a medium as a part of a treatment plan.

When the processor 54 determines that there is a treatment beam break during the treatment session, the processor 54 then transmits one or more control signals to stop the delivery of the treatment beam 26. The processor 54 also transmits one or more control signals to operate the imaging system 30 so that the source 32 delivers diagnostic radiation during the beam break to obtain image data, and to read out the image data from the imager 34 (Step 206). As shown in FIG. 4A, an image pulse chart 410, and an image acquisition chart 412 are aligned with the treatment beam pulse chart 400. The image pulse chart 410 represents when diagnostic radiation is to be delivered by the imaging system 30. The acquisition chart 412 represents when image data are to be read out from the imager 34. As shown in the figure, the delivery of imaging radiation by the imaging source 32, and the collection of image data from the imager 34, occur during the treatment beam breaks.

In some embodiments, during an image data acquisition period, the processor 54 may operate on the gantry 12, and/or the collimator 28, to prepare the system 10 for delivering a next treatment beam. For example, the processor 54 may transmit a control signal that causes the gantry 12 to rotate from a first gantry angle to a second gantry angle. In such cases, the treatment beam break occurs between the first and second gantry angles, and the imaging system 30 may be operated to obtain image data during any part(s) of such beam break as the gantry 12 rotates from the first gantry angle to the second gantry angle. When the treatment source 20 reaches the second gantry angle (which corresponds to an end of the treatment beam break), the processor 54 then stops the operation of the imaging system 30. The processor 54 then operates the treatment source 20 to deliver treatment beam to continue treating the patient 16 in accordance with the treatment plan.

The acts of delivering treatment radiation (Step 202), determining treatment beam break (Step 204), and delivering diagnostic radiation to obtain image data during the treatment session (Step 206) are repeated (as represented by arrow 207), until sufficient image data for reconstruction of an image have been obtained.

Figure 3A:
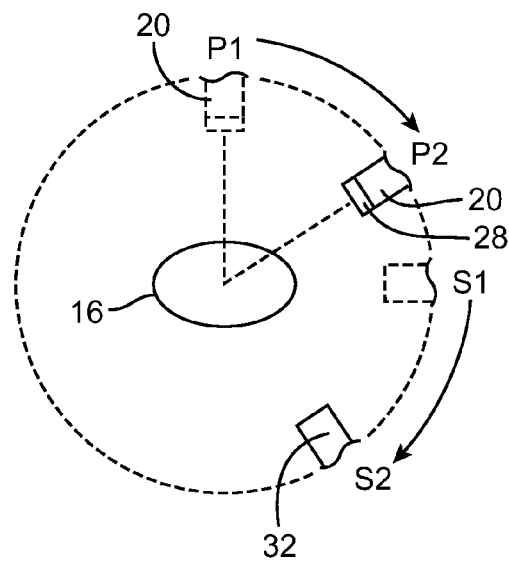
FIG. 3A-3D illustrate a concept of planned beam breaks in a treatment session.

FIGS. 3A-3D illustrate the above concept. FIG. 3A shows the treatment source 20 delivering treatment radiation to treat the patient 16 in accordance with a treatment plan. The treatment source 20 is configured to rotate from position P1 to position P2, during which, treatment radiation is being delivered. In the illustrated embodiments, the imaging source 32 is coupled to a same gantry 12 as the treatment source 20, and so rotation of the imaging source 32 also causes the imaging source 32 to rotate. Thus, as the treatment source 20 rotates from P1 to P2, the imaging source 32 also rotates from S1 to S2. Since the processor 54 is configured to cause the imaging system 30 to deliver diagnostic radiation only during treatment beam break, no diagnostic radiation is being delivered as the imaging source 32 moves from S1 to S2.

Figure 3B:
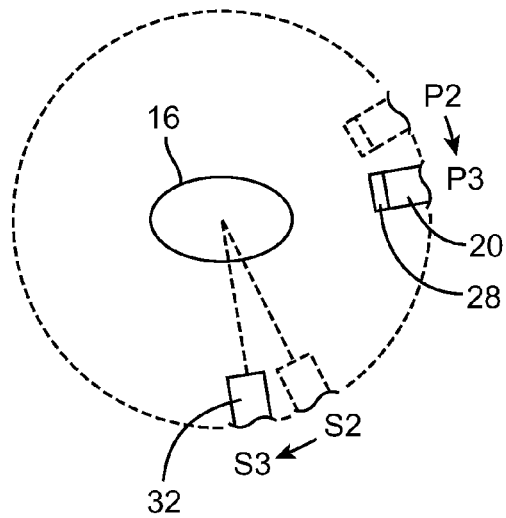

As shown in FIG. 3B, the treatment source 20 is prescribed by the treatment plan to move from gantry position P2 to position P3, during which no treatment radiation is to be delivered. For example, during the movement of the treatment source 20 from P2 to P3, the collimator 28 may be operated to change its configuration for a next treatment beam delivery. As the treatment source 20 rotates from P2 to P3, the imaging source 32 also rotates from position S2 to position S3. During the treatment beam break that occurs when the imaging source 32 is moving from S2 to S3, the processor 54 may operate on the imaging system 30 to generate image data at one or more gantry angles. In some embodiments, the processor 54 is configured to detect an end of a treatment beam delivery (e.g., beginning of a beam break), and automatically operates the imaging source 32 to obtain image data after the beam break begins.

Figure 3C:
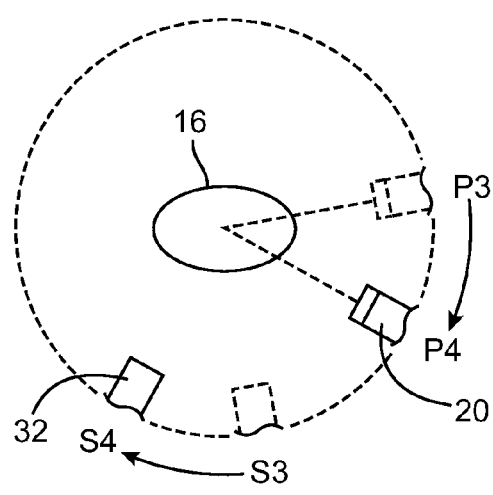

In the illustrated example, the treatment plan also prescribes that treatment radiation is to be delivered from gantry position P3 to position P4. Thus, when the treatment source 20 reaches position P3, the processor 54 stops the operation of the imaging system 30, and operates on the treatment source 20 to deliver treatment radiation from position P3 to P4 (FIG. 3C). In some embodiments, the processor 54 is configured to detect an end of a beam break, and automatically operates the treatment source 20 to deliver treatment radiation after the beam break ends. While the treatment source 20 rotates from position P3 to P4, the imaging source correspondingly rotates from position S3 to S4. However, the imaging source does not deliver diagnostic radiation between positions S3 and S4 because the processor 54 is configured to cause the imaging source to deliver diagnostic radiation only during treatment beam breaks in the illustrated example.

Figure 3D:
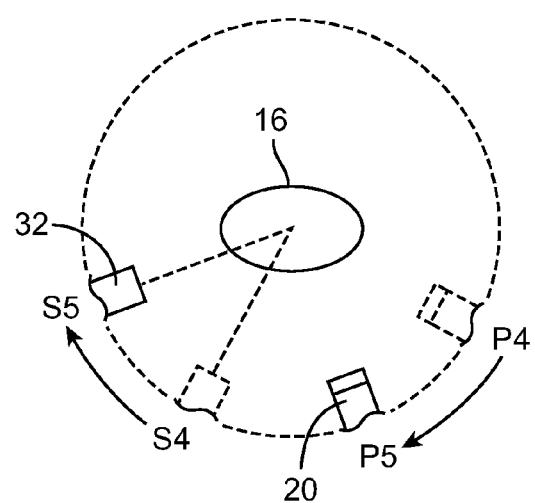

As shown in FIG. 3D, the treatment source 20 is prescribed by the treatment plan to move from gantry position P4 to position P5, during which no treatment radiation is to be delivered. For example, during the movement of the treatment source 20 from P4 to P5, the collimator may be operated to change its position for a next treatment beam delivery. As the treatment source 20 rotates from P4 to P5, the imaging source 32 also rotates from position S4 to position S5. During the treatment beam break that occurs when the imaging source 32 is moving from S4 to S5, the processor 54 may operate on the imaging system 30 to generate additional image data at one or more gantry angles.

When sufficient image data have been obtained for reconstruction of an image, the processor 54 then uses the image data to reconstruct an image during the treatment session (Step 208). For example, it may be the case that the image data obtained when the imaging source 32 rotated from position S2 to S3 are not sufficient for reconstruction of an image. However, when the additional image data are obtained from gantry position S4 to position S5, then the processor 54 may determines that the amount of image data are sufficient for reconstruction of an image. In such cases, the processor 54 (or another processor) then determines an image using at least some of the image data that have been obtained.

In the illustrated embodiments, the reconstructed image is a tomosynthesis image. As used in this specification, the term "tomosynthesis image" refers to an image created using a number of projection images in a back projection technique, wherein the number of projection images (input images) is less than that in a set that is required for a CT image reconstruction, and/or the trajectory of source and detector is less restricted than that used in a CT imaging procedure. For the purpose of this definition, the term "projection image" covers x-ray transmission projection images, as well as projection images generated from emission of particles. Also, in some embodiments, for the purpose of this definition, a set of images that is required for CT image reconstruction is considered to include images (e.g., 300 or more) generated over a range of gantry rotation that is 180° plus the fan beam angle. In some embodiments, the projection images for constructing a tomosynthesis image are taken over an angular range, which is a value between 1° and an angular range value X that is less than that needed for a complete projection set for CT imaging (e.g., with X being 180° plus the fan angle), wherein the number of projection images generated in this range is a value that is between 1-1000 (e.g., 2). In other embodiments, the projection images for constructing a tomosynthesis image are taken over an angular range, which is a value between 5° and 45°, wherein the number of projection images generated in this range is a value that is between 5-100. In other embodiments, the reconstructed image may be a CT image, such as a volumetric CT image, or a subset of a volumetric CT image, such as a two-dimensional slice of a CT image. Techniques for reconstruction of an image using image data, such as CBCT reconstruction algorithms and tomosynthesis reconstruction algorithms, are well known in the art, and therefore will not be described in detail.

Figure 5:
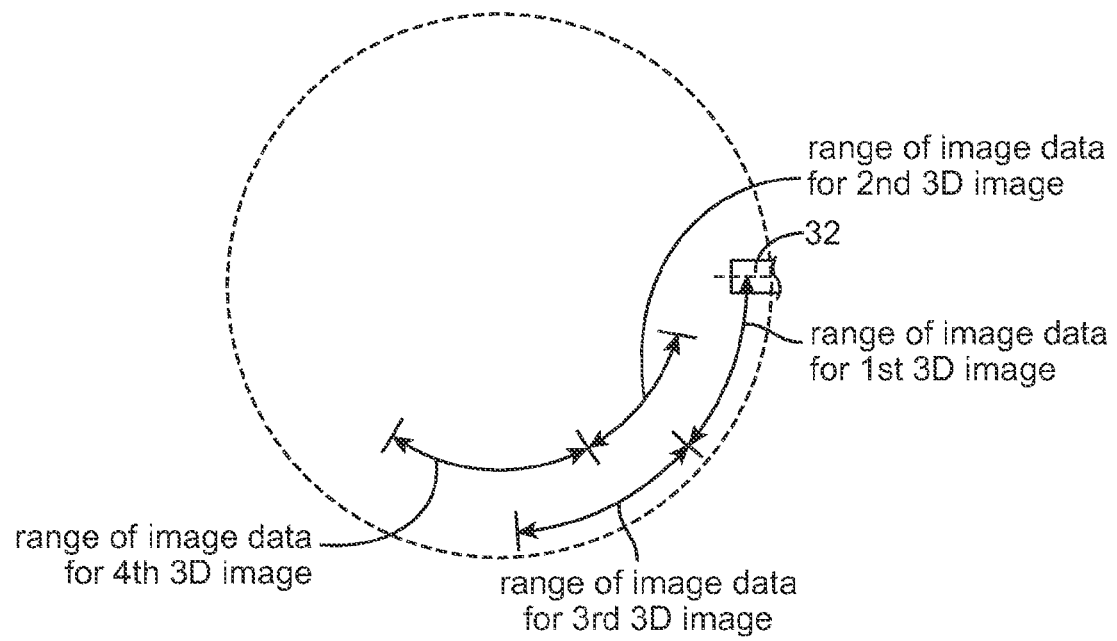
FIG. 5 illustrates a technique for obtaining reconstructed images during a treatment session in accordance with some embodiments.

In some embodiments, the processor 54 is configured to reconstruct an image using image data that have been obtained in the most recent prescribed range of gantry angles. For example, the prescribed range of gantry angles may be 20°, in which cases, the processor is configured to reconstruct an image as soon as enough projections are acquired, e.g., after 20° of gantry rotation. Then the treatment and image acquisition may be continued, e.g., for another 10° of gantry rotation (now the gantry has moved 30°), and the processor then reconstruct another image using the most recently collected image data in the last 20° gantry range, and so on (FIG. 5). This way, one can obtain an image set (that includes image data generated within 20° of gantry rotation) for every 10° of gantry rotation. As shown in FIG. 5, four images are reconstructed, with each image being formed using data generated within 20° of gantry rotation. The images are separated from each other by 10° of gantry rotation. In other embodiments, the gantry range for each image may be different from 20°. Also, in other embodiments, the reconstructed images may be separated from each other by a vale other than 10°.

Figure 6:
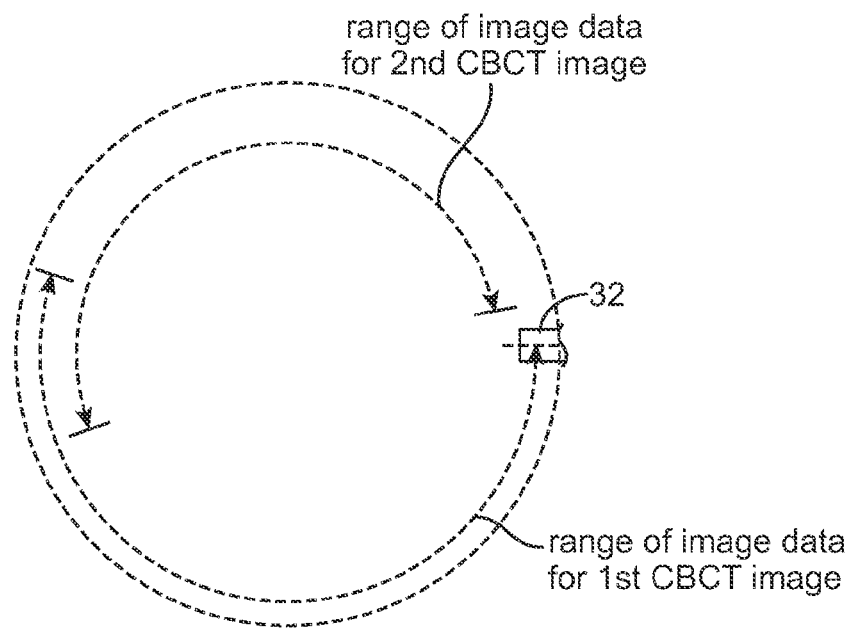
FIG. 6 illustrates a technique for obtaining reconstructed CBCT images during a treatment session in accordance with some embodiments.

In another example, the processor may be configured to reconstruct a cone-beam CT (CBCT) image as soon as enough projections are acquired, e.g., after 200°. Then the treatment and image acquisition may be continued, e.g., for another 100° of gantry rotation (now the gantry has moved 300°), and the processor then reconstruct another CBCT image using the most recently collected image data in the last 200° gantry range, and so on (FIG. 6). This way, one can gather a CBCT image set (that includes image data generated within 200° of gantry rotation) for every 100° of gantry rotation.

The reconstructed image(s) obtain during the treatment session may be used for a variety of purposes. In some embodiments, the reconstructed image(s) may allow an operator or a software (such as an image analysis tool) to monitor the position and/or accuracy of the treatment volume over the course of the treatment. The reconstructed image may also allow the system 10 to interrupt the treatment procedure if the operator or the software detects that the position of a target is not the same as, or not within a prescribed tolerance from, a planned position. In some cases, the processor 54 may also automatically make correction of the target volume position based on the reconstructed image(s).

In other cases, the processor 54 may also be configured to automatically modify the treatment plan based at least in part on the reconstructed image(s). For example, the processor 54 may be configured to correct target volume position, radiation field size, radiation field shape, and/or radiation dose based on information from the reconstructed image(s). In some cases, the processor 54 may compare the reconstructed image(s) with reference image(s), and modify the treatment plan based on such comparison. In further embodiments, instead of automatically modifying the treatment plan, the processor 54 may display the reconstructed image(s) (e.g., together with a planned image) on a computer screen, thereby allowing an operator to make changes to the treatment plan during the treatment session. In other embodiments, the processor 54 may be configured to stop a treatment beam based on information from the reconstructed image(s). For example, if the reconstructed image indicates that the target volume is out of a specified tolerance, then the processor 54 may generate a signal to stop the treatment beam. In any of the embodiments described herein, the reconstructed image(s) may be stored in a medium, so that it can be retrieved later, e.g., for processing, analysis, etc.

As illustrated in the above embodiments, because the reconstructed image is obtained during the treatment session, the reconstructed image can accurately represent the current condition and configuration of the internal organs of the patient 16 while the patient 16 is being treated. Also, because the reconstructed image (e.g., a tomosynthesis image or a CT image) can provide a detail delineation of the internal organs, a physician and/or a processor can better access the condition of the patient 16 as the treatment is being carried out during the treatment session. Also, as illustrated in the above embodiments, the beam off time during the planned beam breaks (which was previously considered useless) is used to obtain image data. Thus, the time that the beam is off is not completely lost, and is utilized favorably (i.e., to obtain information about the state of the patient 16) during the treatment session.

Figure 4B:
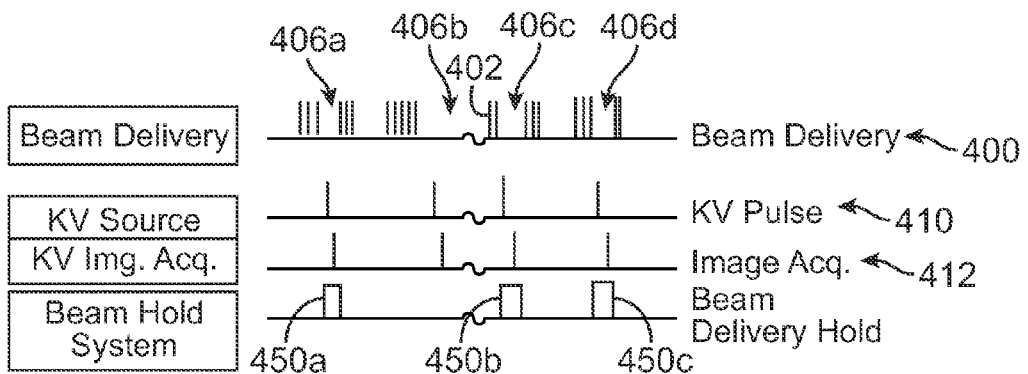
FIG. 4B illustrates a technique for acquiring image data during a treatment session using planned beam breaks and enforced beam breaks.

In other embodiments, in addition or in alternative, to obtaining image data during treatment beam break(s), the system 10 may be configured to obtain image data during enforced beam break(s). As used in this specification, the term "enforced beam break" refers to a beam break that is imposed specifically for obtaining image data. FIG. 4B illustrates such concept. In particular, FIG. 4B illustrates an example of a treatment beam pulse chart 400, which may be derived from a treatment plan. As shown in the figure, the treatment beam pulses 402 represent treatment beam that is prescribed in the treatment plan to be delivered at certain gantry angles. An image pulse chart 410, and an image acquisition chart 412 are aligned with the treatment beam pulse chart 400. As shown in the figure, the treatment plan provides certain treatment beam breaks 406a-406d that allow image data to be acquired during certain gantry movements. However, it may be determined that treatment beam breaks 406a, 406c, 406d need to be enforced. In such cases, the beam hold system may provide enforced beam breaks 450a, 450b, 450c to enforce the period and/or gantry angles during which images may be acquired. Such may be desirable in some embodiments in which the treatment beam break, or a part of the treatment beam break, is desired to be enforced during a treatment session. For example, in some cases, an original treatment plan may need to be modified, either before the treatment session (e.g., during treatment planning), or during the treatment session, in order to minimize the effect of enforced beam breaks. In such cases, the enforced beam break(s) would allow image data to still be acquired at certain desired gantry position(s), without negatively effecting the desired dose distribution, despite the modified treatment plan. In any of the embodiments described herein, the enforced beam break(s) may be stored in a medium as part of the treatment plan.

Also, in some cases, additional beam break(s) may be needed between the treatment beam breaks such that image data may be obtained at certain gantry angle(s). In such cases, an enforced beam break may be imposed, which allows image data to be obtained between the treatment beam breaks. Various techniques may be used to impose enforced beam break(s). In some embodiments, one or more enforced beam breaks may be imposed evenly between two treatment beam breaks to achieve a desired beam break distribution. For example, assuming that it is desirable to have at least one beam break at every 30° of gantry rotation (i.e., the prescribed image acquisition rate is at least one per 30° gantry angle), and assuming that two treatment beam breaks exist in a treatment plan that are 100° apart (e.g., there is a treatment beam duration that starts at gantry angle 20° and ends at gantry angle 120°). In such example, three enforced beam breaks EB1, EB2, EB3 may be imposed at gantry angles 45°, 70°, 95°, respectively, thereby resulting in beam breaks that are spaced evenly and no further than the prescribed image acquisition rate (i.e., 30° in the example). In other embodiments, the enforced beam breaks need not be spaced evenly. For example, the three enforced beam breaks EB1, EB2, EB3 may be imposed at gantry angles, 45°, 75°, 105°, respectively.

In some embodiments, the determination of the enforced beam break(s) may be performed before a treatment session. In such cases, before a treatment session begins, the treatment plan is analyzed to determine if additional beam break(s) need to be imposed so that a desired number of projection data and/or a desired distribution of projection data can be obtained. The enforced beam break(s) may be accepted as a part of the treatment plan, in which cases, the enforced beam break(s) become respective planned beam break(s). In some cases, after the enforced beam break(s) is determined, the treatment dose distribution due to the effect of the enforced beam break(s) may be evaluated, and the treatment plan may be further optimized. For example, it may be the case that due to an addition of an enforced beam break, less treatment radiation may be delivered during a particular gantry range. In such cases, the treatment plan may be modified such that sufficient treatment radiation is delivered to compensate for the lost of dose.

In other embodiments, the determination of the enforced beam break(s) may be performed in real time, e.g., by the processor 54, during the treatment session. For example, during the treatment session, the processor 54 may keep track of an amount of rotation that has been gone through by the gantry 12 since the last imaging radiation was delivered or since the last image read-out. If the tracked gantry rotation exceeds a prescribed threshold, the processor 54 then imposes an enforced beam break in real time by generating a signal to stop the delivery of the treatment beam, and operates the imaging system 30 to acquire image data. In other embodiments, in addition to, or in the alternative of, gantry rotation, the imposing of the enforced beam break may be performed based on other criteria. For example, in other embodiments, the processor 54 may keep track of a period that has lapsed since the last imaging radiation was delivered or since the last image read-out. If the tracked period exceeds a prescribed threshold, the processor 54 then imposes an enforced beam break in real time by generating a signal to stop the delivery of the treatment beam, and operates the imaging system 30 to acquire image data.

Providing enforced beam break(s) is advantageous. This is because in some situations, a certain amount of image projections is needed in order to obtain a reconstructed image with desirable image quality. The enforced beam break(s) allow a desired amount of image data to be obtained within a given gantry range, thereby ensuring that the reconstructed image will have a desirable image quality. In some embodiments, in order to minimize the influence of the imaging system (e.g., its enforced beam breaks) to the treatment delivery, the system 10 may be configured to initially attempt to acquire image projection during only the planned beam breaks. In such cases, the system 10 would utilize enforced beam break(s) when it determines that the planned beam breaks are not sufficient to acquire a desired amount of image data for image reconstruction purpose.

Figure 4C:
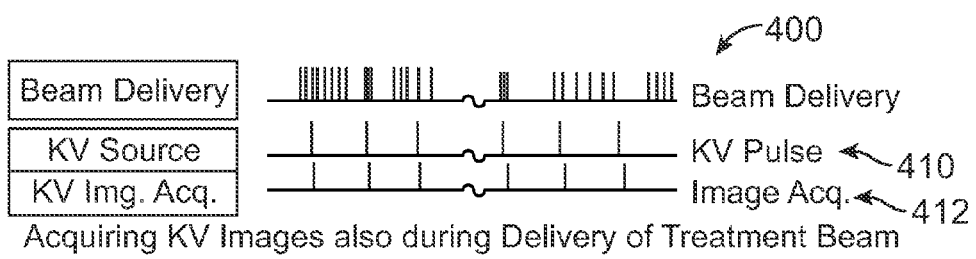
FIG. 4C illustrates a technique for acquiring image data during a delivery of treatment beam in a treatment session.

In the above embodiments, the obtaining of the image data is performed during beam break(s). In other embodiments, the image data may be obtained simultaneously with a delivery of treatment radiation. For example, as shown in FIG. 4C, imaging radiation may be delivered by the imaging source 32 during a delivery of treatment radiation. This is advantageous in that it allows the imaging system 30 to obtain image data during any part(s) of the treatment session, and does not limit the acquisition of image data to during beam break(s).

In the above embodiments, the method 200 has been described with reference to the treatment source 20 rotating in one direction. However, in other embodiments, the treatment source 20 may rotate back and forth—e.g., as in an arc treatment. In such cases, the processor 54 may operate the imaging system 30 to obtain image data when the gantry 12 is moving in both the directions. In further embodiments, the treatment source 20 may not move in a circular path. For example, in other embodiments, the treatment source 20 may move in a rectilinear path, an elliptical path, or a spiral path. In any of these cases, the treatment source 20 may move in one direction along the path, or in a back-and-forth manner along the path.

In the above embodiments, the treatment source 20 and the imaging source 32 are coupled to a same gantry so that movement of the treatment source 20 is coupled with corresponding movement of the imaging source 32. In other embodiments, the treatment source 20 and the imaging source 32 may be moveable independently of each other. For example, the treatment source 20 may be coupled to a first ring at the gantry 12, and the imaging source 32 may be coupled to a second ring at the gantry 12. Each of the rings may lie in respective planes that are parallel (or alternatively, non-parallel) to each other. During the method 200, the imaging source 32 may be moved independently from the treatment source 20. Such feature may be desirable in that the gantry positions at which the imaging source 30 generates image data are not affected by the position of the treatment source 20. Thus, the imaging source 32 may be moved to any desired positions during the treatment session for obtaining image data. However, the timing for generating diagnostic radiation is still controlled by the beam break(s) in the illustrated embodiments.

In other embodiments, instead of having the treatment source 20 and the imaging source 32 move independently in respective planes that are parallel to each other, the treatment source 20 and the imaging source 32 may move independently in respective planes that are non-parallel to each other. FIG. 7A illustrates a robotic arm system 700 that includes a first arm 702 carrying the imaging source 32, and a second arm 704 carrying the imager 34. During use, the first and second arms 702, 704 may be rotated to turn the imaging source 32 and the imager 34 about an isocenter 710. FIG. 7B shows the robotic arm system 700 with the imaging source 32 and the imager 34 rotated to another position that is different from that in FIG. 7A. In the figure, the robotic arm system 700 is illustrated looking down from the treatment source 20 (from a beam's eye view). Thus, in the illustrated embodiments, the plane of rotation by the imaging source 32 and the imager 34 is perpendicular to a plane of rotation by the treatment source 20. However, in other embodiments, the plane of rotation by the imaging source 32 and the imager 34 needs not be perpendicular to, and may form other angles with, the rotation plane of the treatment source 20. Also, in any of the embodiments described herein, the robotic arm system 700 may be part of a device (e.g., a positioning system, or an imaging system 30) that is configured to translate in three degrees of freedom (e.g., along respective X, Y, and Z axes) so that the point of rotation may align with an isocenter of a treatment machine.

FIG. 8 illustrates another imaging system 30 that may be used to collect image data during a treatment session in accordance with the method 200. In the illustrated embodiments, the imaging source 32 and the imager 34 are configured to translate relative to the isocenter 710 via a linear slider mechanism 900. Also, in the illustrated embodiments, the imaging system 30 may further include a collimator 902 for modulating the imaging beam so that a desired beam field size is directed to a desired position at the imager 34. In some cases, the imaging source 32 may also be configured to rotate (as represented by arrow 910) so that the imaging beam can be aimed towards a desired direction. In other embodiments, if the range of movement by the source 32 and the imager 34 is small, then the imaging source 32 needs not be configured to rotate, and the aiming of the imaging beam may be accomplished using the collimator 902. In the figure, the system 30 is illustrated looking down from the treatment source 20 (from a beam's eye view). Thus, in the illustrated embodiments, the movement of the imaging source 32 and the imager 34 is within a plane that is perpendicular to a plane of rotation by the treatment source 20. However, in other embodiments, the plane of movement by the imaging source 32 and the imager 34 needs not be perpendicular to, and may form other angles with, the rotation plane of the treatment source 20. Also, in any of the embodiments described herein, the system 30 may be configured to translate in three degrees of freedom (e.g., along respective X, Y, and Z axes) so that the operative position of the imaging system 30 may align with an isocenter of a treatment machine.

During use, the imaging source 32 and the imager 34 translate relative the isocenter 710 in opposing directions to generate image data for at least a portion of the patient 16. In the figure, the imaging system 30 is illustrated with the imaging source 32 and the imager 34 in a first operative position to generate a first set of image data, and in a second operative position to generate a second set of image data. In some embodiments, the movement of the source 32 and the imager 34 may be stopped while image data is being acquired. In other embodiments, the source 32 and the imager 34 may be configured to move while image data is being acquired. The generating of the image data is performed during beam break(s) in accordance with the method 200 described herein. The image data may be used to reconstruct image(s) during a treatment session.

Figure 9:
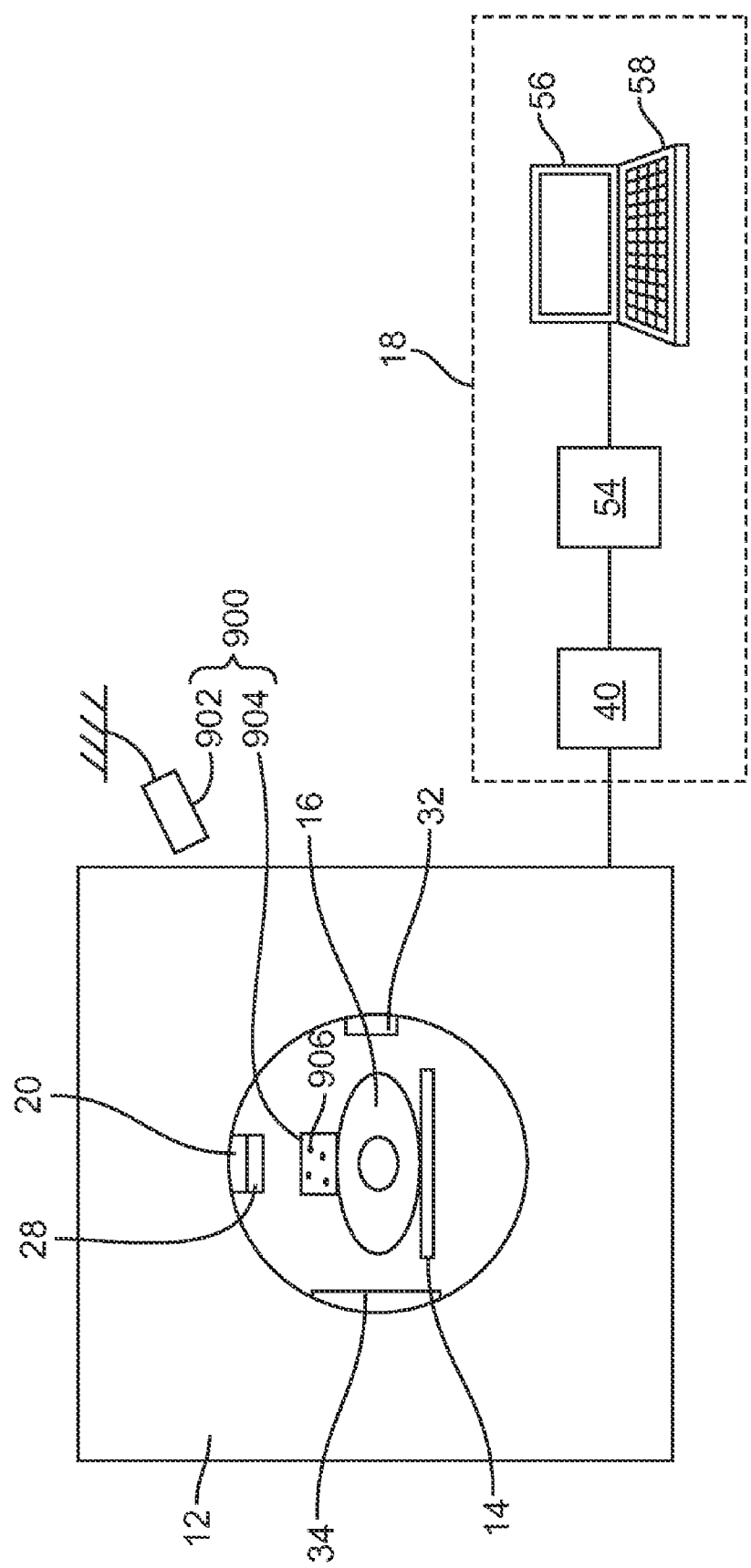
FIG. 9 illustrates a radiation system that includes a position monitoring system in accordance with some embodiments.

The above described embodiments may be suitable for obtaining reconstructed image(s) of a body part that is relatively stationary during treatment. In other embodiments, the method 200 described may also be used to obtain reconstructed image(s) of a body part that is moving during treatment. In such cases, the obtaining of image(s) during the treatment session may take into account a physiological motion, such as a breathing motion, of the patient 16. For example, in any of the embodiments described herein, the breathing motion of the patient 16 may be monitored by a position sensing device, and the image is reconstructed in the method 200 by using image data that are generated in a same phase or amplitude, or within a same phase or amplitude range. FIG. 9 illustrates a patient position sensing system 900 in accordance with some embodiments. The patient position sensing system 900 includes an optical device 902 and a marker block 904. In the illustrated embodiments, the optical device 902 is a camera (a CCD), such as a CCD camera, but can be other type of optical or radio frequency (RF) sensor that is capable of sensing an object (e.g., to determine relative and/or absolute motion in space). The optical device 902 can be mounted to a ceiling, to the radiation system 10, to the patient support 14, or to a support stand (not shown). The marker block 904 includes a plurality of markers 906 that are so positioned such that at least some of them can be viewed/sensed by the optical device 902. The markers 906 can be implemented using reflective objects. In the case of positioning using RF technique, radio frequency transponders may be placed on the patient or implanted into the patient. In the illustrated embodiments, the optical device 902 is coupled to the processor 54, which analyzes signals from the optical device 902. Alternatively, the optical device 902 can be coupled to another processor, for processing image signals received from the optical device 902, or other types of device (e.g., RF based sensor).

During use, the marker block 904 may be placed on the patient's 16 chest, and the patient 16 is allowed or instructed to breath. As the patient 16 is breathing, the marker block 904 will correspondingly move up and down. While the patient 16 is breathing, the optical device 902 views the marker block 904, and transmits image signals to the processor 54. The processor 54 analyzes the image signals to identify the markers 906 and determine their positions. From the positions of the markers 906, the processor 54 determines the position of the marker block 904. As a result, as the patient 16 is breathing, the processor 54 can determines the positions of the marker block 904, which correspond to breathing amplitudes or phase of the patient 16.

In the illustrated embodiments, the processor 54 may associate a determined position of the marker block 904 with a certain phase of a breathing cycle. As used in this specification, the term "phase" refers to a variable that is associated with a degree of completeness of a physiological cycle (e.g., a respiratory cycle). For example, if the block 904 is determined to be at position (or has an amplitude of) 2.4 cm, then the processor 54 may determine that the patient 16 is at an end of an inhale phase. On the other hand, if the block 904 is determined to be at position (or has an amplitude of) 0.4 cm, then the processor 54 may determine that the patient 16 is at an end of an exhale phase. In some embodiments, the phase of a breathing cycle may be expressed as a variable with a value that ranges between 0° and 360°, with 0° representing a beginning of a breathing cycle, and 360° representing an end of a breathing cycle.

In other embodiments, instead of using the marker block 904, other types of marker(s) may be used. For example, in other embodiments, one or more external markers may be directly coupled to the patient 16 without using a block. In other embodiments, one or more landmark(s) on the patient 16 may function as marker(s). In other embodiments, the position and/or movement may be monitored by an optical surface contouring system (e.g., with laser or structured light, etc). In further embodiments, internal marker(s) may be used. The internal marker(s) may be device(s) that is implanted inside the patient 16. Alternatively, one or more landmark(s) inside the patient 16 may function as internal marker(s). If internal marker(s) is used, then the optical device 902 is not needed. Instead, another imaging device, such as a fluoroscopic X-ray device, a MRI device, or a radio frequency device, etc., may be used to view the internal marker(s) in real time. The viewed internal marker(s) is then used to correlate the marker(s) position with a phase of a physiological motion.

Figure 10:
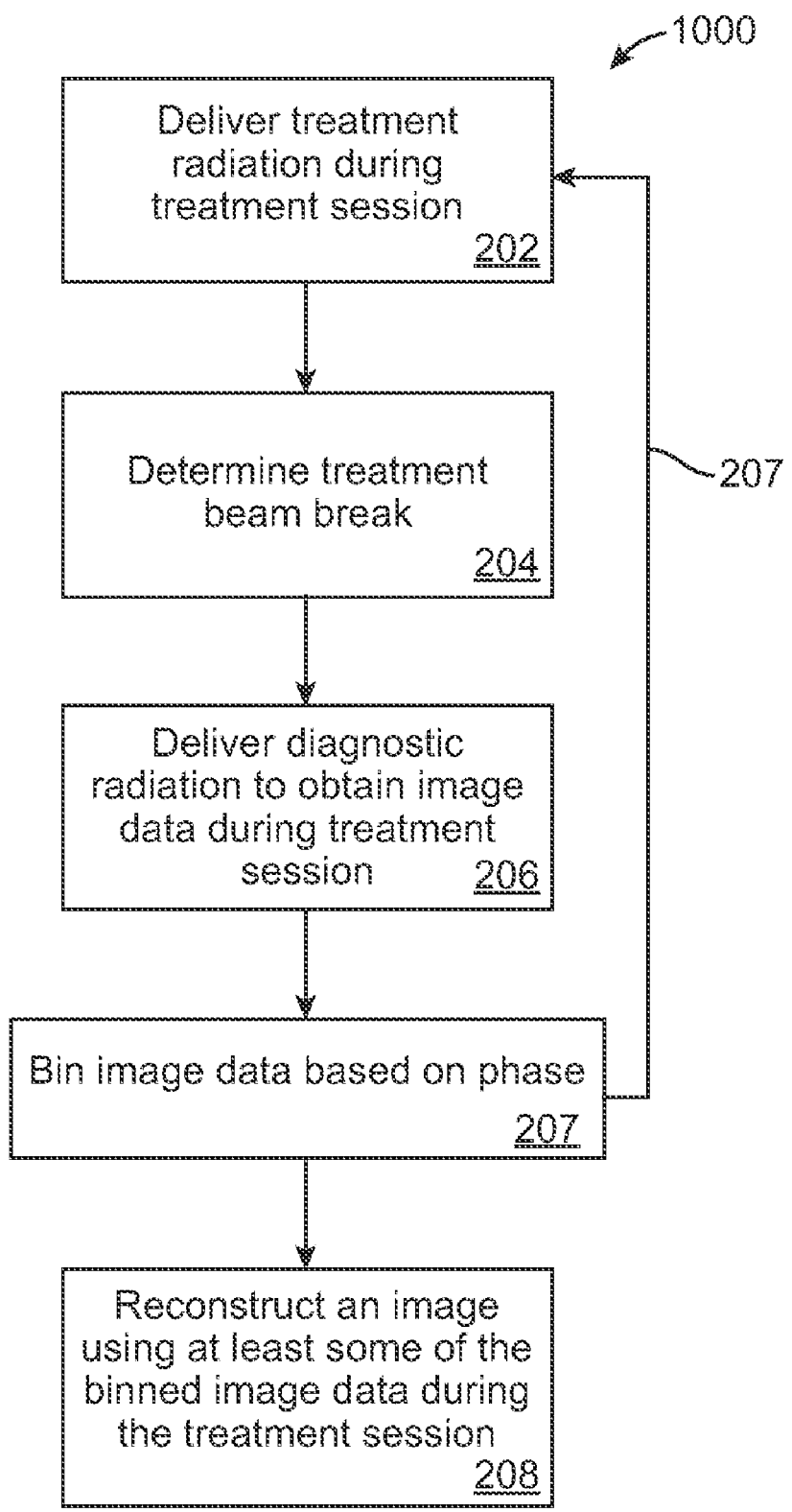
FIG. 10 illustrates a method of performing an imaging procedure during a treatment procedure in accordance with other embodiments.

FIG. 10 illustrates a method 1000 for obtaining an image during a treatment session in accordance with some embodiments. The method 1000 is the same as the method 200 except that it considers patient movement. In some embodiments, when using the system 10 to generate image data during beam break(s), the processor 54 is configured to determine a phase of a physiological cycle at which the image data is generated, and associate the determined phase with the image data, thereby binning the image data based on the determined phase (Step 207 in FIG. 10). In such cases, when the processor 54 reconstructs an image in step 208, the processor 54 selects only image data that are generated at the same phase or within a same prescribed phase range. For example, if image data D1, D4, D6, D8 (generated at different respective gantry angles) are all generated within a prescribed phase range of 25° to 30°, then the processor 54 will use these image data to reconstruct an image for that prescribed phase range. The number of prescribed phase range may be arbitrary set to any numbers. For example, in some cases, four prescribed phase ranges may be used, i.e., phase range 1 is from 0° to 90°, phase range 2 is from 90° to 180°, and phase range 3 is from 180° to 270°, and phase range 4 is from 270° to 390°. In another example, the number of phase range may be 10 or more. In the illustrated embodiments, the processor 54 may reconstruct different images for different prescribed phase ranges. The reconstructed images may be stored in a medium, and/or may be displayed in a sequence to form a video showing how an organ moves during the physiological cycle.

The reconstructed image(s) for the respective phase(s) obtain during the treatment session may be used for a variety of purposes. In some embodiments, the reconstructed image(s) may allow an operator or a software (such as an image analysis tool) to monitor the position and/or accuracy of the treatment volume over the course of the treatment. The reconstructed image may also allow the system 10 to interrupt the treatment procedure if the operator or the software detects that the position of a target is not the same as, or not within a prescribed tolerance from, a planned position. In some cases, the processor 54 may also automatically make correction of the target volume position based on the reconstructed image(s). In other cases, the processor 54 may also be configured to automatically modify the treatment plan based at least in part on the reconstructed image(s). For example, the processor 54 may be configured to correct target volume position, radiation field size, radiation field shape, and/or radiation dose based on information from the reconstructed image(s). In further embodiments, instead of automatically modifying the treatment plan, the processor 54 may display the reconstructed image(s) (e.g., together with a planned image) on a computer screen, thereby allowing an operator to make changes to the treatment plan during the treatment session. In other embodiments, the processor 54 may be configured to stop a treatment beam based on information from the reconstructed image(s) and the corresponding phase(s). For example, if the reconstructed image indicates that the target volume is out of a specified tolerance, then the processor 54 may generate a signal to stop the treatment beam. In any of the embodiments described herein, the reconstructed image(s) may be stored in a medium, so that it can be retrieved later, e.g., for processing, analysis, etc.

In any of the embodiments described herein, the operation of the imaging system 30 may be based on input from the position sensing system 900. For example, in some cases, the processor 54 may determines during the treatment session that certain image data for a particular phase are desired to be obtained. In such cases, the position sensing system 900 continues to monitor the breathing of the patient 16, and transmits signals that are related to the breathing motion of the patient 16 to the processor 54. The processor 54 continues to determine the breathing phases of the patient 16 as the patient 16 is breathing. When the processor 54 determines that a particular phase for which image data is desired to be obtained is coming up or has reached, the processor 54 then implements an enforced beam break to obtain image data for that phase. Such may be accomplished by the processor 54 transmitting one or more signals to stop the delivery of treatment beam when the desired phase has reached (or close to being reached). The imaging system 30 is then used to obtain image data.

Patient movement during radiation delivery may significantly affect the outcome of the procedure. For example, in a radiation treatment procedure, patient movement affects dose distribution in patient. One method of controlling this phenomenon is to use gated treatment. In gated treatment, treatment radiation is only delivered while patient is in a position or phase (e.g., breathing phase) that is prescribed for radiation delivery. For example, in a treatment plan, the radiation may be prescribed to be delivered only when the patient is relatively stationary (e.g., when the patient is in full inhale or exhale positions) for some period of time, and when there are not any unnecessary critical organs that would receive radiation when a target in the patient is radiated. In any of the embodiments described herein the processor 54 may be configured to receive information regarding a breathing phase or position of the patient 16, and operate the radiation system 10 to deliver treatment radiation towards the patient 16 in synchronization with the breathing of the patient 16. For example, the processor 54 may generate one or more signals to move the radiation source 20, move the collimator leaves, rotate and/or swivel the collimator (e.g., about one or more axes), scan a different area (e.g., by changing a beam direction while maintaining at a gantry angle), move the patient support 14, or any combination of the foregoing, in synchronization with the breathing of the patient 16. The breathing monitoring system 900 and the processor 54 track the breathing behavior of the patient 16 as treatment radiation is being delivered.

It should be noted that the device for monitoring breathing of the patient 16 is not limited to the monitoring system 900 described, and that other monitoring system, or combination of monitoring systems, may be used in other embodiments. For example, in other embodiments, strain gauge, distance sensor(s) using ultrasound, RF detection/measurement, or other devices known in the art, may be used to monitor physiological movement of the patient 16.

In some embodiments, while the imaging system 30 is being operated to obtain image data, the part of the system 10 for delivering treatment radiation is not completely deactivated. For example, the radiation source 20 may be operated to stop the delivery of radiation, but other components of the radiation system 10 may remain activated so that the radiation system 10 is in a state in which it is ready for delivering additional treatment radiation. This is advantageous in that it allows treatment radiation to be delivered quickly as soon as the imaging system 30 finishes obtaining image data during a particular beam break, without having to go through significant idling time that may result from the startup and initialization of the treatment component of the radiation system 10 if the treatment component of the radiation system 10 is completely deactivated.

In some embodiments, while the imaging system 30 is being used to generate image data, the system 10 is in a state in which the system 10 is capable of automatically delivering additional radiation upon a detection of one or more desired conditions. For example, in some embodiments, a desired condition for delivering additional radiation may be an end of a beam break, in which case, when the end of a beam break is reached, the system 10 automatically delivers additional radiation towards the patient 16. In another example, the position or the physiological phase of the patient may be monitored (e.g., using the monitoring device 900). In such cases, the system 10 automatically delivers additional treatment radiation when the patient is at a desired physiological phase (e.g., breathing phase) or a desired position (e.g., breathing position). In some embodiments, the processor 54 may be configured to receive information regarding a position or a physiological phase of the patient from the monitoring device 900. During use, when the processor 54 detects that image data has been obtained by the imaging system 30 (e.g., end of a beam break), and when the processor 54 determines that the desired patient position or physiological phase has been reached, the processor 54 then generates a signal to cause the system 10 to deliver additional radiation. In some embodiments, the system 10 includes a button (e.g., a safety button), wherein when the button is un-pressed, the system 10 is prevented from delivering radiation. In such cases, the system 10 may be configured to automatically deliver additional treatment radiation by having a user press the button while the treatment source 20 is not delivering radiation, such that when the desired condition(s), such as, end of a beam break, achievement of a desired position or physiological phase by the patient, etc., for delivering additional treatment radiation is detected (e.g., by the processor 54), the system 10 can automatically deliver the additional treatment radiation without having to wait for additional input from the user. In other cases, the system 10 may not include a safety button, and the system 10 may be configured to automatically deliver additional treatment radiation by configuring the processor 54 to generate a signal to cause the system 10 to deliver additional radiation when the desired condition(s) is detected.

As discussed, in some embodiments, imaging radiation may be delivered by the imaging source 30 during a delivery of the treatment radiation. In such cases, when obtaining image data, it may be desirable to reduce or minimize the effects by the treatment radiation that does not originate from the image source 32. Sometimes, even for the embodiments in which the imaging radiation is delivered during beam break(s), it may be desirable to remove undesirable effect due to scatter radiation from the treatment beam delivered prior to a beam break, and/or radiation leakage from the treatment source 20 (e.g., leakage of radiation between leaves of collimator 28).

Various techniques may be used to reduce or minimize the effects by radiation (e.g., treatment radiation) not originating from the imaging source 32. In some embodiments, a x-ray scatter-rejection-grid may be used. The x-ray scatter-rejection-grid is configured to absorb radiation which does not originate from the direction of the imaging source 32. In some embodiments, the x-ray scatter-rejection-grid may be a focused grid in which the grid lamellas are angled such that they are pointing towards the imaging source's focal point. In other embodiments, the x-ray scatter-rejection-grid may include parallel grids which are not focused. X-ray scatter-rejection-grids are known in the art, and therefore, will not be described in further detail.

In some cases, the pixels which are light sensitive photo-diodes are in blocking direction under a small voltage so they act as capacitors (as in the case of amorphous silicon imagers), which can be discharged by light. In other embodiments, the imager pixels may be flushed to have a defined imager pixel value. For example, in some embodiments, a light pulse may be used to illuminate the image sensors from the back periodically or between image acquisitions (e.g., right before a delivery of imaging radiation) such that the imager pixels are periodically set to a defined state, which is not dependant from the previous radiation levels. In other embodiments, a current may be driven in a forward direction through the pixels to thereby set all of the pixels to a defined state.

In other embodiments, the imaging dose may be increased to overcome the higher background noise resulted from the radiation that originates form the treatment source 20. The radiation may be from radiation leakage, from scattered treatment radiation anywhere in the system 10 (like the collimator 28 or patient support 14, etc.), from scattered treatment radiation from the patient 16 itself, or from secondary radiation introduced by the treatment radiation somewhere along the beam path. In some embodiments, the imaging dose may be increased by providing an imaging (e.g., kV) beam pulse using higher voltage or current. In other embodiments, the imaging dose may be increased by providing a longer imaging beam pulse. In further embodiments, the imaging dose may be increased by using higher voltage or current, and using longer beam pulse.

In other embodiments, signal resulted from the treatment beam scatter, stray, and leakage radiation may be subtracted out. For example, in some embodiments, the signal resulted from leakage radiation and/or scatter radiation is read out as background. Then when the imaging source 32 generates image signal later, the background signal is subtracted from the image signal.

In other embodiments, the imager 14 may be placed in an optimal position so that undesirable effect due to scatter and/or radiation leakage may be minimized or at least reduced. Sometimes, a detector position that is further away from a scatter source, such as a treatment volume, is less sensitive to effects of stray and scatter radiation of the treatment beam. Thus, in some embodiments, the detector may be placed as far away as possible from the scatter source.

In other embodiments, image processing may be used to remove, or at least reduce, effects of scatter, stray, leakage radiation, and beam pulse. For example, if the imaging system 30 acquires an image while the treatment beam is on, then the resulting image may include a bright line that corresponds with the treatment beam pulse. In some cases, the processor 54 may be configured to detect such effect in the image, and correct it out. For example, the processor 54 may be configured to erase that line, and replace it with pixels that are obtained by averaging the neighboring pixels. In other embodiments, the expected scatter and/or leakage behavior may be determined during treatment planning (e.g., pre-calculated from simulation and/or calculated from measured information). In such cases, the actual scatter and/or leakage may be compensated for based on the expected scatter and/or leakage. For example, it may be determined during treatment planning that obtaining image data at a certain gantry angle while the treatment beam is on would result in a certain expected amount of scatter radiation. In such cases, during the actual treatment session, if image data is obtained at the same gantry angle while the treatment beam is on, then the processor 54 will automatically subtract the predetermined (which may be determined by simulation and/or calculation, etc.) expected amount from the actual signals.

In other embodiments, the image acquisition may be synchronized to the radiation treatment pulses. In some cases, the system 10 may be configured to read out a defined number of imager's 34 pixel lines a prescribed time after a treatment beam pulse. For example, if reading out one pixel line takes 30 micro seconds, and the time between treatment beam pulses is 2.5 milliseconds, then the system 10 may be configured to read 75 lines, wait for the next treatment beam pulse, then read the next 75 lines, etc. Such technique provides a better defined behavior of the imager 34, and would prevent a reading out of the image signals during a treatment beam pulse. Also, such technique allows any corrections or compensations of the undesirable effects due to the treatment beam to be performed in a more stable and predictable manner.

It should be noted that any of the above techniques (x-ray scatter-rejection-grid, setting imager pixels to a defined state, increasing imaging dose, subtracting out signal resulted from the treatment beam scatter, stray, and leakage radiation, placing imager at optimal position, image processing to remove effect of scatter and radiation leakage, and synchronizing the image acquisition to the radiation treatment pulses) may be combined in other embodiments.

In any of the embodiments described herein, the imaging source 32 may be integrated with the treatment source 20. Such may be accomplished by using a dual energy source (such as that described with reference to FIG. 1B), in which one energy is used for generating a treatment beam, and another energy is used for generating a diagnostic beam. Such configuration may be desirable because it allows a beam's eye view image in the direction of the treatment source 20 (or in a direction close to the treatment source 20—e.g., plus or minus 5°) to be obtained. Alternatively, the imaging source 32 and the treatment source 20 may be placed adjacent to each other, e.g., in a side-by-side configuration. Such configuration is desirable in that it also allows an image in the beam's eye view to be generated without reconstructing a volumetric image. Also, the resulting image directly corresponds with the treatment view because it is generated in a plane that is approximately perpendicular to the treatment beam's axis. Thus, the resulting image may be used for a variety of purposes, including but not limited to determining and/or verifying target tissue's position, shape, and orientation, determining and/or verifying critical organ's position, shape, and orientation, obtaining dose information, etc. Furthermore, because a three-dimensional is not needed to be reconstructed, the resulting beam's eye view image may be obtained relatively quickly (e.g., at least faster than the time required to reconstruct a three-dimensional image). It should be noted that the act of obtaining the beam's eye view image may be performed at any time during the treatment session. For example, in some embodiments, the beam's eye view image may be obtained at any time during the method 200, such as, right before the delivery of treatment beam (before Step 202), right after a delivery of the treatment beam (after Step 202), periodically during a treatment session in which the method 200 is being performed, etc. In other embodiments, the act of obtaining the beam's eye view image may be performed during any treatment session, including treatment session that may not involve the method 200.

In any of the embodiments described herein, a beam's eye view image may be reconstructed from image data (projections) captured not in the beam's eye view. This allows monitoring of the treatment target from the treatment beam direction without having an imaging system in the beam's eye direction (e.g., without having an imaging source next to the treatment source, and/or without having an imager opposite from the treatment source). In some cases, the beam's eye image may be displayed in a screen for allowing an operator to see the image of the target region from the treatment beam's direction. Reconstruction of the image from the beam's eye view also allows monitoring of the treatment target while the treatment radiation beam is scanned or modulated by a multi-leaf collimator. The reconstruction of the beam's eye view image may be performed before a treatment session, during a treatment session (e.g., at any time during the method 200), or after a treatment session.

Figure 11:
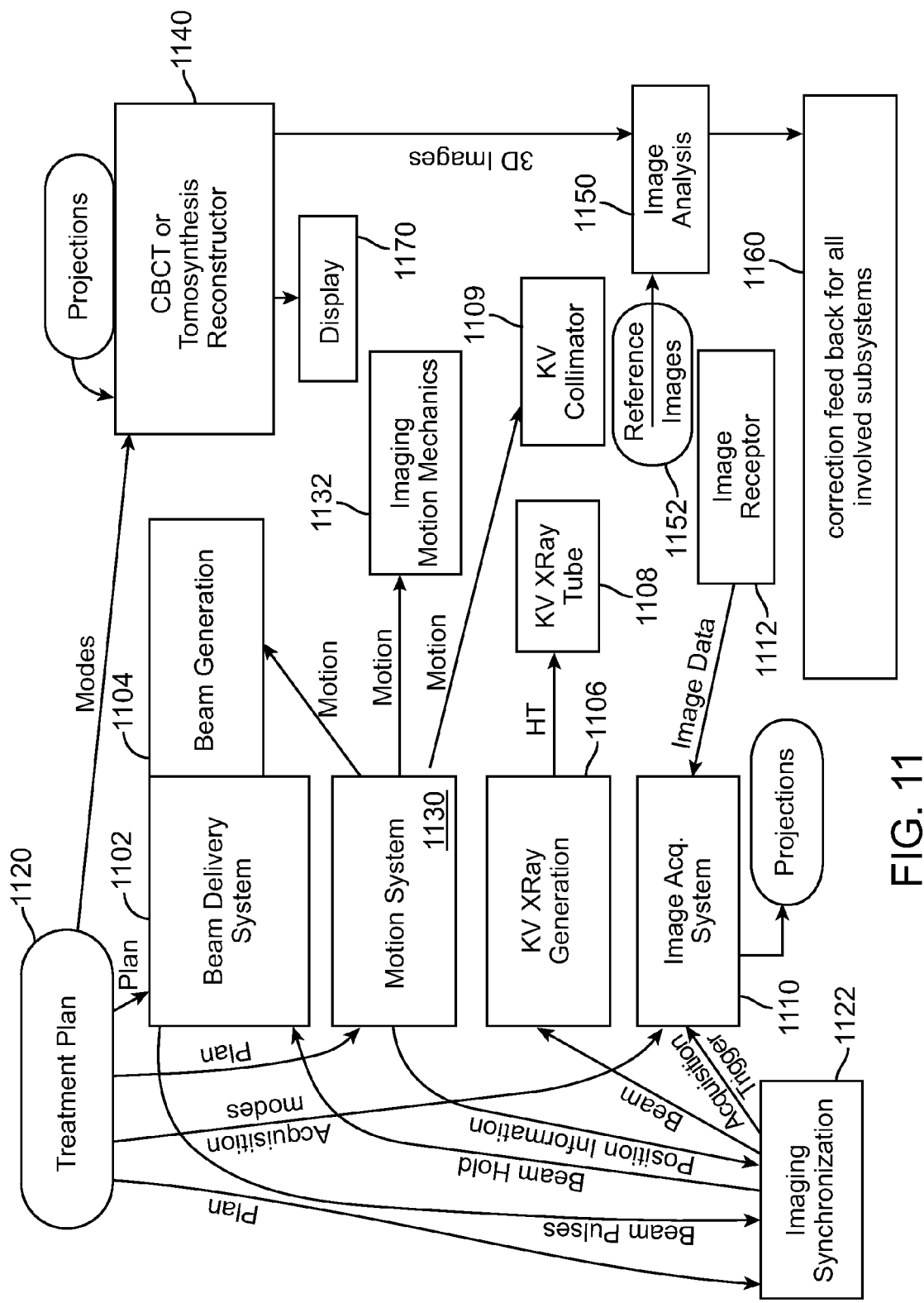
FIG. 11 illustrates a block diagram of a treatment system that includes an imaging system in accordance with some embodiments.

FIG. 11 illustrates a block diagram showing various components of the system 10 in accordance with some embodiments. In particular, the diagram illustrates the synchronization between the various components for obtaining reconstructed image during a treatment session. As shown in the figure, the system 10 includes a treatment beam delivery system 1102 that comprises a treatment beam source 1104, an imaging source 1106 that includes a x-ray tube 1108, and an image acquisition system 1110 that includes an imager 1112. In some cases, the imaging source 1106 may be considered to be a part of the image acquisition system 1110.

The system 10 also includes a treatment plan 1120, whose information is used to operate the beam delivery system 1102, the imaging source 1106, and the image acquisition system 1110. For example, the treatment plan 1120 may prescribe the condition for delivering treatment beam using the beam delivery system 1102. The treatment plan 1120 may also prescribe the condition for delivering imaging beam using the imaging source 1106, and for acquiring (e.g., generating and/or reading out) the image signals using the image acquisition system 1110.

The system 10 also includes a image reconstructor 1140 (e.g., a CBCT or tomosynthesis image reconstructor), which is configured to process projection image data from the image acquisition system 1110 to obtain reconstructed image(s) during a treatment session. The treatment plan 1120 may prescribe certain condition for operating the image constructor 1140. For example, the treatment plan 1120 may prescribe the image reconstructor 1140 to reconstruct an image at certain prescribed gantry angle, when a certain prescribed amount of image data has been acquired, and/or how often to reconstruct an image.

The reconstructed image(s) may be displayed in a display 1170, so that a physician or an operator can visualize and/or study the image(s). In some embodiments, the reconstructed image(s) may also be processed by an image analysis module 1150, which analyzes the image(s). The result of the analysis may be used by a feedback module 1160, which may modify the treatment plan 1120, and/or control any of the components in the figure based on the result of the analysis. In some embodiments, the image analysis module 1150 may be configured to compare the reconstructed image(s) with reference image(s) 1152. In such cases, the operation of the feedback module 1160 may be based on a result of the comparison. For example, the feedback module 1160 may modify the treatment plan 1120, and/or control any of the components in the figure based on the result of the comparison.

In some embodiments, the system 1110 may optionally include a motion/position sensing system 1130 for monitoring the positions of the patient 16 during the treatment session. The system 1110 also includes an imaging system motion mechanism 1132 for placing the imaging source or receptor to a desired imaging position. In some cases, this imaging position may be determined in advance and be stored as a part of the treatment plan 1120. The system 1130 may be configured to transmit information regarding a patient's position/motion to the treatment source 1104 (or the treatment beam delivery system 1102), which then gates the delivery of treatment beam based on the information. In some embodiments, if the imaging system also includes a collimator 1109, the system 1130 may also operate the collimator 1109 based on the position/motion of the patient 16, and/or the position/motion of the imaging components (e.g., source, imager, etc.) relative to the position of the patient 16.

As shown in the figure, the system 10 further includes an image synchronization module 1122. The image synchronization module 1122 is configured to process the treatment plan 1120, and control the various components (e.g., the beam delivery system 1102, the imaging source 1106, the image acquisition system 1110, etc.) of the system 10 based on information from the treatment plan 1120, so that the acquisition of the image data during treatment can be coordinated with the delivery of treatment radiation. For example, if it is determined from the treatment plan 1120 that there is a beam break, then the imaging synchronization module 1122 would transmit a signal to the beam delivery system 1102 to stop the delivery of treatment beam, and operate the imaging source 1106 and the imaging acquisition system 1110 to obtain image data.

In some embodiments, the imaging synchronization module 1122 also controls the image reconstructor 1140 based on the treatment plan. For example, the treatment plan 1120 may prescribe that an image be reconstructed at certain prescribed gantry angle, when a certain prescribed amount of image data has been acquired, and/or how often to reconstruct an image. In such cases, the imaging synchronization module 1122 transmits a signal to the reconstructor 1140 accordingly to carry out the imaging task prescribed by the treatment plan 1120.

In some embodiments, the imaging synchronization module 1122 also receives information from the beam delivery system 1102, and controls other components based on such information. For example, the beam delivery system 1102 may transmit signals to the imaging synchronization module 1122 to indicate number of treatment beam pulses that have been delivered. In some cases, the treatment plan 1120 may prescribe that if the number of treatment beam pulses exceeds a certain number, and/or if there has not been any image acquisition for a certain prescribed period, then the imaging synchronization module 1122 may implement an enforced beam break to obtain image data.

In some embodiments, the imaging synchronization module 1122 may also receive information regarding the patient's 16 position/motion from the system 1130. The module 1122 may utilize such information to control the various components of the system 10. For example, the module 1122 may control the beam delivery system 1102 to gate the delivery of the treatment beam. The module 1122 may also control the imaging source 1106 and the image acquisition system 1110 so that image data for a prescribed phase of a physiological cycle are obtained. In addition, the module 1122 may control the image reconstructor 1140 so that image data that correspond to the same phase or same phase range are used to reconstruct an image for that phase or phase range.

It should be noted that any of the components illustrated in FIG. 11 may be combined with another component, and that any of the components may be divided into subcomponents. Also, in other embodiments, the system 10 needs not have all of the components shown, and any of the components may not be included in the system 10.

Computer System Architecture

Figure 12:
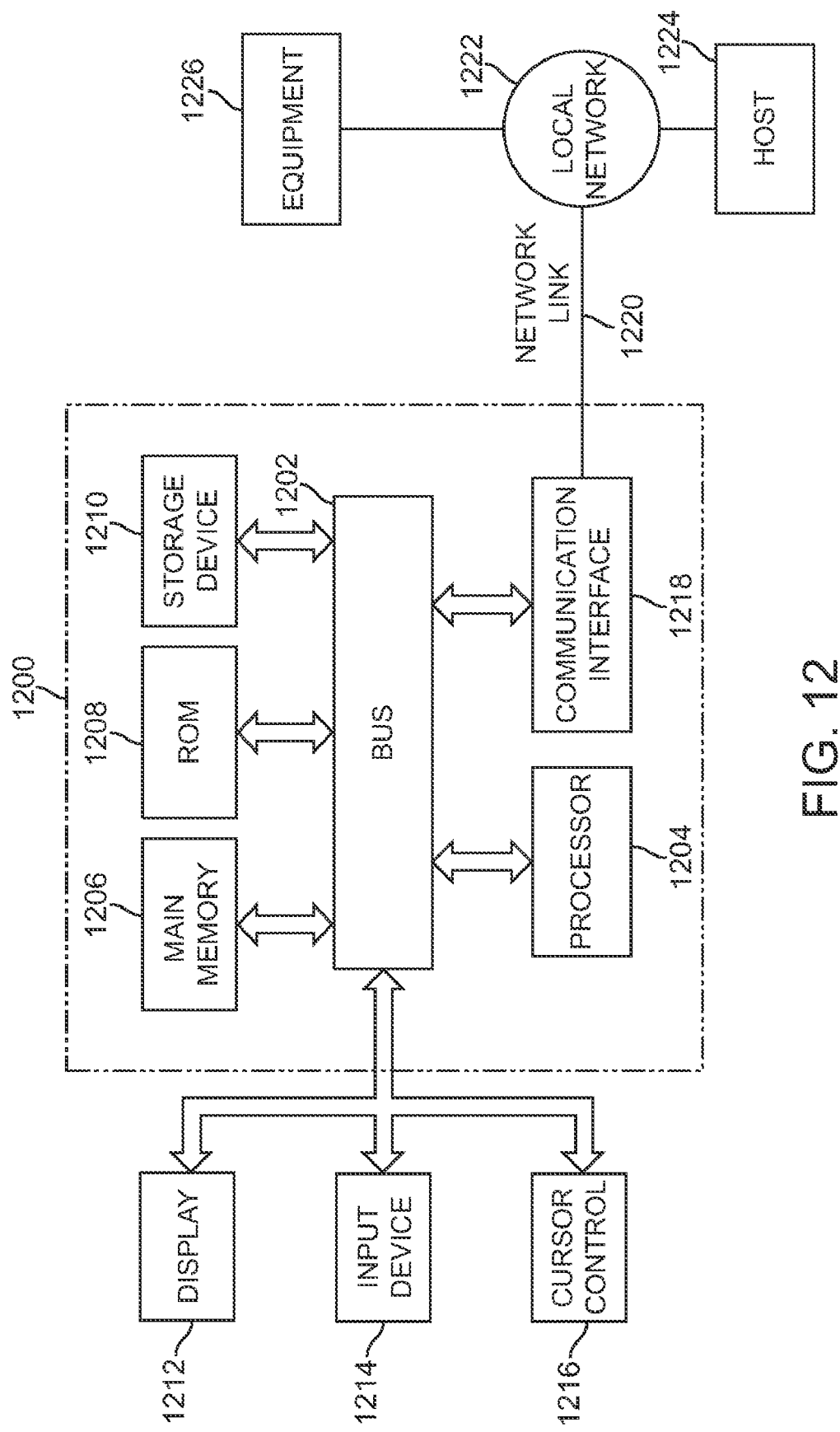
FIG. 12 is a block diagram of a computer system architecture, with which embodiments described herein may be implemented.

FIG. 12 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT) or a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Volatile media includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although particular embodiments have been shown and described, it will be understood that they are not intended to limit the present inventions, and it will be obvious to those skilled in the art that various changes and modifications may be made without departing from the spirit and scope of the present inventions. For example, the term "image" as used in this specification needs not be limited to image that is displayed, and may refer to image data that is not displayed for viewing, such as image data that is stored in a medium. The specification and drawings are, accordingly, to be regarded in an illustrative rather than restrictive sense. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A medical system, comprising:
   a radiation treatment system having a treatment radiation source configured to deliver treatment radiation during a treatment session;
   an imaging system configured to obtain image data during the treatment session; and
   a processor configured to determine a beam break, and automatically operate the imaging system to obtain the image data during the beam break;
   wherein the radiation treatment system includes a component that remains activated while the imaging system obtains the image data during the beam break.

2. The medical system of claim 1, wherein the processor is configured to determine an image using at least some of the image data, wherein the image has an image plane that is perpendicular to an axis of the treatment radiation source.

3. The medical system of claim 1, wherein the beam break comprises a treatment beam break.

4. The medical system of claim 1, wherein the beam break comprises an enforced beam break.

5. The medical system of claim 1, wherein the processor is configured to cause the imaging system to obtain additional image data during an additional beam break, wherein the beam break and the additional beam break comprise a plurality of treatment beam breaks, a plurality of enforced beam breaks, or a treatment beam break and an enforced beam break.

6. The medical system of claim 1, wherein the imaging system has a diagnostic radiation source that is capable of moving relative to the treatment radiation source.

7. The medical system of claim 1, wherein an operation of the treatment radiation source is synchronized with an operation of the imaging system.

8. The medical system of claim 1, wherein the processor is configured for reconstruction of an image using at least some of the image data during the treatment session.

9. The medical system of claim 8, wherein the at least some of the image data comprises most recent image data that are obtained within a prescribed time or prescribed gantry angle range.

10. The medical system of claim 8, wherein the reconstructed image comprises a beam's eye view image that corresponds with a position of the treatment radiation source.

11. The medical system of claim 10, wherein the at least some of the image data for the beam's eye view image comprises projection image data, wherein none of the projection image data is obtained at a direction of the treatment radiation source.

12. The medical system of claim 8, wherein the reconstructed image comprises a tomosynthesis image.

13. The medical system of claim 1, wherein the beam break is predetermined and is included in a treatment plan, and wherein the processor is configured to determine the predetermined beam break by processing the treatment plan.

14. The medical system of claim 1, wherein the radiation treatment system is configured to move the treatment radiation source during the beam break to a position prescribed by a treatment plan for delivering the treatment radiation, and wherein the processor is configured to automatically operate the imaging system to obtain the image data during the beam break while the treatment radiation source is being moved.

15. A medical system, comprising:
   a treatment radiation source configured to deliver treatment radiation during a treatment session;
   an imaging system configured to obtain image data during the treatment session; and
   a processor configured to determine a beam break, and automatically operate the imaging system to obtain the image data during the beam break;
   wherein the beam break comprises an enforced beam break, and wherein the processor is configured to determine the enforced beam break by:
   determining a period that has lapsed since a last image data acquisition;
   comparing the period with a prescribed threshold; and
   determining the enforced beam break based at least in part on the comparison.

16. A medical system, comprising:
   a treatment radiation source configured to deliver treatment radiation during a treatment session;
   an imaging system configured to obtain image data during the treatment session; and
   a processor configured to determine a beam break, and automatically operate the imaging system to obtain the image data during the beam break;
   wherein the beam break comprises an enforced beam break, and wherein the processor is configured to determine the enforced beam break by:
   determining a gantry angle undergone by a gantry since a last image data acquisition;
   comparing the gantry angle with a prescribed threshold; and
   determining the enforced beam break based at least in part on the comparison.

17. A medical system, comprising:
   a treatment radiation source;
   an imaging system configured to automatically obtain image data in a beam break that occurs during a treatment session; and
   a processor configured to automatically operate the treatment radiation source to deliver treatment radiation during the treatment session after the beam break ends.

18. The medical system of claim 17, wherein the processor is configured to determine an image using at least some of the image data, wherein the image has an image plane that is perpendicular to an axis of the treatment radiation source.

19. The medical system of claim 17, wherein the beam break comprises a treatment beam break.

20. The medical system of claim 17, wherein the beam break comprises an enforced beam break.

21. The medical system of claim 17, wherein the processor is configured to cause the imaging system to obtain additional image data during an additional beam break, wherein the beam break and the additional beam break comprise a plurality of treatment beam breaks, a plurality of enforced beam breaks, or a treatment beam break and an enforced beam break.

22. The medical system of claim 17, wherein the imaging system has a diagnostic radiation source that is capable of moving relative to the treatment radiation source.

23. The medical system of claim 17, wherein an operation of the treatment radiation source is synchronized with an operation of the imaging system.

24. The medical system of claim 17, wherein the processor is configured for reconstruction of an image using at least some of the image data during the treatment session.

25. The medical system of claim 24, wherein the at least some of the image data comprises most recent image data that are obtained within a prescribed time or prescribed gantry angle range.

26. The medical system of claim 24, wherein the reconstructed image comprises a beam's eye view image that corresponds with a position of the treatment radiation source.

27. The medical system of claim 26, wherein the at least some of the image data for the beam's eye view image comprises projection image data, wherein none of the projection image data is obtained at a direction of the treatment radiation source.

28. The medical system of claim 23, wherein the reconstructed image comprises a tomosynthesis image.

29. The medical system of claim 17, wherein the beam break is predetermined and is included in a treatment plan, and wherein the processor is configured to determine the predetermined beam break by processing the treatment plan.

30. The medical system of claim 17, wherein the treatment radiation source is a part of a radiation treatment system, and wherein the radiation treatment system includes a component that remains activated while the imaging system obtains the image data during the beam break, so that the radiation treatment system is in a state during the beam break in which it is ready for delivering the treatment radiation.

31. The medical system of claim 17, wherein the treatment radiation source is a part of a radiation treatment system, and wherein the radiation treatment system is configured to move the treatment radiation source during the beam break to a position prescribed by a treatment plan for delivering the treatment radiation, and wherein the imaging system is configured to automatically obtain the image data in the beam break while the treatment radiation source is being moved.

32. A medical system, comprising:
a treatment radiation source;
an imaging system configured to automatically obtain image data in a beam break that occurs during a treatment session; and
a processor configured to automatically operate the treatment radiation source to deliver treatment radiation during the treatment session after the beam break ends;
wherein the beam break comprises an enforced beam break, and wherein the processor is configured to determine the enforced beam break by:
determining a period that has lapsed since a last image data acquisition;
comparing the period with a prescribed threshold; and
determining the enforced beam break based at least in part on the comparison.

33. A medical system, comprising:
a treatment radiation source;
an imaging system configured to automatically obtain image data in a beam break that occurs during a treatment session; and
a processor configured to automatically operate the treatment radiation source to deliver treatment radiation during the treatment session after the beam break ends;
wherein the beam break comprises an enforced beam break, and wherein the processor is configured to determine the enforced beam break by:
determining a gantry angle undergone by a gantry since a last image data acquisition;
comparing the gantry angle with a prescribed threshold; and
determining the enforced beam break based at least in part on the comparison.

* * * * *